United States Patent [19]

Durant et al.

[11] 4,219,553

[45] Aug. 26, 1980

[54] ALKOXY PYRIDYL SUBSTITUTED ALKANES

[75] Inventors: Graham J. Durant; Charon R. Ganellin, both of Welwyn Garden City; George S. Sach, Welwyn, all of England

[73] Assignee: Smith Kline & French Laboratories Limited, Welwyn Garden City, England

[21] Appl. No.: 948,616

[22] Filed: Oct. 4, 1978

Related U.S. Application Data

[62] Division of Ser. No. 816,420, Jul. 18, 1977, Pat. No. 4,139,624.

[51] Int. Cl.$^2$ .......................................... C07D 239/24
[52] U.S. Cl. .................................. 424/250; 424/251; 544/238; 544/333; 544/405
[58] Field of Search ...................... 544/333, 238, 405; 424/251, 250

[56] References Cited

U.S. PATENT DOCUMENTS

| | | | |
|---|---|---|---|
| 3,968,227 | 7/1976 | Durant et al. | 424/273 |
| 4,070,472 | 1/1978 | Durant et al. | 424/263 |
| 4,137,319 | 1/1979 | Durant et al. | 424/263 |
| 4,139,624 | 2/1979 | Durant et al. | 424/263 |

*Primary Examiner*—Nicholas S. Rizzo
*Attorney, Agent, or Firm*—Joan S. Keps; Richard D. Foggio; William H. Edgerton

[57] ABSTRACT

The compounds are $C_2$–$C_8$ straight chain alkanes terminally substituted, symmetrically or unsymmetrically, by N-(N'-substituted guanidino), N-(N',N"-disubstituted guanidino), N-(N'-substituted thioureido), N-(nitromethylene amidino) or S-(N-substituted isothioureido)groups. Two compounds of the invention are 1,3-bis-[N'-(2-(3-methoxy-2-pyridylmethylthio)ethyl)-guanidino]propane and 1-[N-(2-(3-methoxy-pyridylmethylthio)ethyl)guanidino]-3-[N'-2-(5-methyl-4-imidazolylmethylthio)ethyl)guanidino]propane. The compounds of this invention are inhibitors of H-2 histamine receptors.

5 Claims, No Drawings

ALKOXY PYRIDYL SUBSTITUTED ALKANES

This is a division of application Ser. No. 816,420 filed July 18, 1977, now U.S. Pat. No. 4,139,624.

This invention relates to new compounds having pharmacological activity. These compounds are inhibitors of H-2 histamine receptors. In addition, this invention relates to pharmaceutical compositions comprising these compounds and to methods of inhibiting H-2 histamine receptors by administering these compounds. The compounds of this invention can exist as the addition salts but, for convenience, reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines", of which mepyramine, diphenhydramine and chlorpheniramine are typical examples, are mediated through histamine $H_1$-receptors (Ash and Schild, *Brit. J. Pharmac. Chemother,* 27, 427, (1966)). However, other of the biological actions of histamine are not inhibited by "antihistamines" and actions of this type which are inhibited by a compound described by Black et al. (Nature, 236, 385 (1972)) and called burimamide are mediated through receptors which are defined by Black et al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by "antihistamines". Histamine $H_2$-antagonists are therefore useful, for example, as inhibitors of gastric acid secretion, as anti-inflammatory agents and as agents which act on the cardiovascular system, for example as inhibitors of the effects of histamine on blood pressure. In the treatment of certain conditions for example inflammation and in inhibiting the actions of histamine on blood pressure, a combination of histamine $H_1$- and $H_2$ antagonists is useful.

The compounds of this invention are histamine $H_2$-antagonists. These compounds are represented by Formula 1:

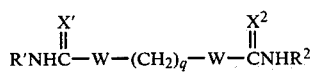  Formula 1 wherein $X'$ and $X^2$, which may be the same or different, are each sulphur, $CHNO_2$ or $NY$ where Y is hydrogen, hydroxy, lower alkyl, cyano or $CONH_2$: $R'$ is a grouping of the structure

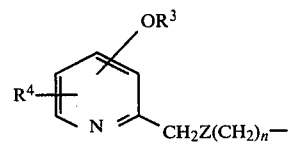

wherein $R^3$ is lower alkyl or $-(CH_2)_pA$ where p is 2 to 4, and A is hydroxy, lower alkoxy or dimethylamino: $R^4$ is hydrogen, lower alkyl, lower alkoxy, amino, halogen, or methylamino; or $-OR^3$ and $R^4$ can together form a $-O(CH_2)_bO-$ group attached to adjacent carbon atoms on the pyridine ring; where b is 1 to 4; Z is sulphur or methylene; n is 2 or 3; $R^2$ has the same scope as $R'$ or is a grouping of the structure:

wherein Het is a nitrogen containing 5 or 6 membered heterocyclic ring such as imidazole, pyridine, thiazole, isothiazole, oxazole, isoxazole, pyrazole, triazole, thiadiazole, pyrimidine, pyrazine or pyridazine which is optionally substituted by lower alkyl, hydroxy, halogen or amino; $Z'$ is sulphur or methylene; $m'$ is 0, 1 or 2; $n'$ is 2 or 3 and the sum of $m'$ and $n'$ is 3, 4; W is NH, and when $X'$ and $X^2$ are both NH, W may also be sulphur; and q is an integer from 2 to 8.

It will be understood that the structure illustrated in Formula 1 is only one of several representations and that other tautomeric forms are also covered by the present invention. Hydrates, pharmaceutically acceptable salts, and hydrated pharmaceutically acceptable salts of compounds of Formula I are also covered by the present invention. Throughout the present specification and claims by the term 'lower alkyl' we mean an alkyl group containing from 1 to 4 carbon atoms.

In a preferred group of compounds $R'$ and $R^2$ are the same, and it is further preferred that Z and $Z'$ are sulphur, m and $m'$ are 1 and n and $n'$ are 2. $R^4$ is preferably hydrogen and $OR^3$ a 3-methoxy or 3-ethoxy group. It is also preferred that $X'$ and $X^2$ are the same, and particularly when $X'$ and $X^2$ are both sulphur, $CHNO_2$, NCH or NH. Most preferably $X'$ and $X^2$ are both NH.

In another preferred group of compounds $R^2$ is such that Het is imidazole, optionally substituted by methyl or halogen, thiazole, isothiazole or pyridine optionally substituted by methyl, methoxy, hydroxyl or halogen.

Compounds of Formula 1 wherein W is NH, and $X'$ and $X^2$ are sulphur, $CHNO_2$, NH, N(lower alkyl), NCN or $NCONH_2$ may be prepared according to scheme 1:

SCHEME 1

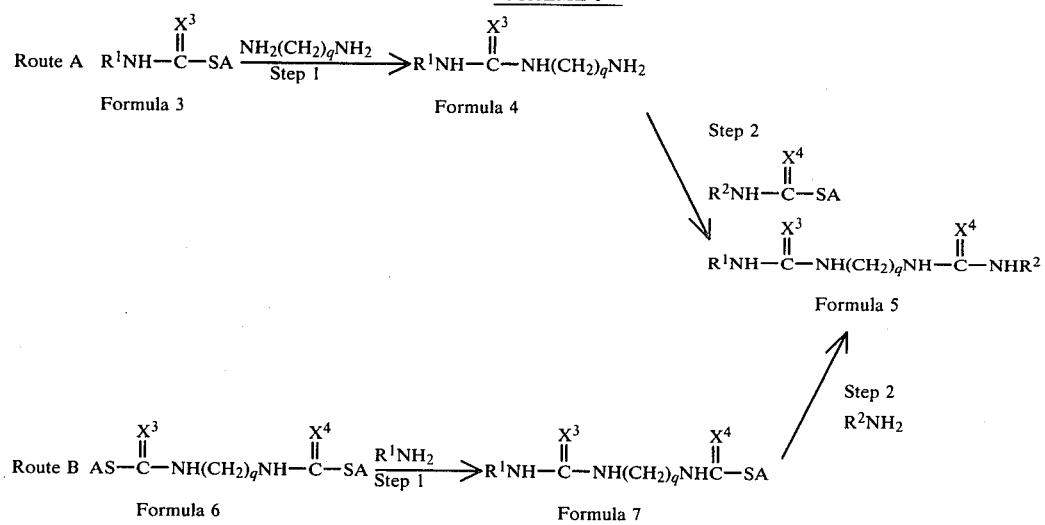

In Scheme 1, A is lower alkyl, $R^1$ and $R^2$, which may be the same or different, are as defined in Formula 1, and $X^3$ and $X^4$, which may be the same or different are sulphur, $CHNO_2$, NH, N (lower alkyl), NCN or $NY^1$ where $Y^1$ is a guanidine protecting group such as benzoyl, benzyloxycarbonyl or ethoxycarbonyl. In Scheme 1 preferably $X^3$ is not NH or N (lower alkyl) unless $R^3$ is the same as $R^4$. Compounds of Formula 1 wherein $X^1$ and $X^2$ are both NH and $R^1$ is not the same as $R^2$ may be prepared by the acid hydrolysis of compounds of Formula 5 wherein $X^3$ and $X^4$ are NCN or N-benzoyl. Compounds of Formula 1 wherein $X^1$ and/or $X^2$ are $CONH_2$ may be prepared by the hydrolysis under mild acid conditions of the corresponding cyanoguanidine of Formula 5 wherein $X^3$ and/or $X^4$ is NCN.

Step 1 of Route A may be carried out in the presence of, or in the absence of, a solvent. Preferably this reaction is carried out using an excess of the amine $NH_2(CH_2)_qNH_2$ as solvent. Preferably Step 2 of Route A is carried out in the absence of a solvent or in the presence of a polar solvent such as a lower alcohol or pyridine. Preferably this reaction is carried out at an elevated temperature, e.g. 100° C. When $R^1$ and $R^2$ are the same and $X^3$ and $X^4$ are the same, Step 1 and Step 2 or Route A may be carried out simultaneously, without isolating the intermediate of Formula 4.

Preferably both steps of Route B are carried out in a polar solvent, such as a lower alcohol or pyridine, and at an elevated temperature, e.g. 100° C. When $R^1$ is not the same as $R^2$ preferably one equivalent of the amine $R^1NH_2$ is used in the first step of Route B and an excess of the amine $R^2NH_2$ is used in the second step.

Compounds of formula $R^1NH_2$ may be prepared by methods described in British Pat. specifications Nos. 1305547, 1338169 and 1421999 and German Offenlegungschrift, No. 2634433.

Compounds of Formula 3 wherein $X^3$ is sulphur may be prepared from an amine of formula $R^1NH_2$ by successive reaction thereof with carbon disulphide and an alkylating agent, such as methyl iodide.

Compounds of Formula 3 wherein $X^3$ is $CHNO_2$, N-benzoyl or NCN may be prepared by treating a compound of Formula 9

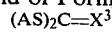

FORMULA 9 wherein $X^3$ is $CHNO_2$, N-benzoyl or NCN, and A is alkyl, with an equivalent amount of an amine of Formula $R^1NH_2$. This reaction is conveniently carried out in a solvent such as ethanol. The compounds of Formula 3 wherein $X^3$ is $CHNO_2$ may alternatively be prepared by treating 1-methylsulphinyl-1-methylthio-2-nitroethylene (described in German Offenlegungschrift 2634430) with an equivalent amount of an amine of Formula $R^1NH_2$.

The compounds of Formula 3 wherein $X^3$ is NH are conveniently prepared by alkylating a thiourea of formula $R^1NHCSNH_2$. These thioureas may be prepared by treating an amine of formula $R^1NH_2$ with benzoyl isothiocyanate, and hydrolysing the product under alkaline conditions.

The compounds of Formula 1 may be prepared by methods analogous to those described for the preparation of compounds of Formula 3.

The compounds of Formula 1 wherein $X^1$ and/or $X^2$ are NY and Y is hydroxy or lower alkyl may be prepared from the corresponding thioureas of Formula 1 wherein $X^1$, and/or $X^2$ are sulphur, and neither $X^1$ nor $X^2$ are NH by alkylating the thiourea, e.g., by treatment with hydrogen chloride in methanol or with methyl iodide, and then treating the resulting isothiourea with hydroxylamine or a lower alkylamine, respectively.

The compounds of Formula 1 wherein $X^1$ and/or $X^2$ are NCN may alternatively by prepared from the corresponding thioureas of Formula 1 wherein $X^1$ and/or $X^2$ are sulphur, and neither $X^1$ nor $X^2$ are NH, by alkylation and treatment of the product with cyanamide and a strong base such as potassium t-butoxide.

The compounds of Formula 1 wherein $X^1$ or $X^2$ are NCN may also be prepared from the corresponding compounds of Formula 2 wherein $X^1$ or $X^2$ are sulphur by reaction of the latter with a heavy metal salt of cyanamide such as lead, mercury or cadmium cyanamide in a solvent such as acetonitrile and/or dimethylformamide.

The compounds of Formula 1 wherein W is sulphur and $X^1$ and $X^2$ are both NH may be prepared by alkylating a thiourea of formula $R^1NHCSNH_2$ wherein $R^1$ is as defined in Formula 2 with a dihaloalkane of formula Hal—$(CH_2)_p$—Hal, wherein Hal represents chlorine, bromine or iodine. Preferably the reaction is carried out on an acid addition salt of the thiourea. Preferably Hal is bromine and the reaction is carried out in a solvent such as ethanol. When $R^1$ is not the same as $R^2$ this reaction will be carried out in two stages. Preferably there will be an excess of the compound of formula Hal—$(CH_2)_p$—Hal in the first stage of the reaction.

The compounds of Formula 2 block histamine $H_2$-receptors, that is they inhibit the biological actions of histamine which are not inhibited by "antihistamines" such as mepyramine but are inhibited by burimamide. For example, the compounds of this invention have been found to inhibit histamine-stimulated secretion of gastric acid from the lumen-perfused stomachs of rats anaesthetized with urethane, at doses of from 0.5 to 256 micromoles per kilogram intravenously. This procedure is referred to in the above mentioned paper of Ash and Schild. The activity of these compounds as histamine $H_2$-antagonists is also demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, in a conventional test, such as the measurement of blood pressure in the anaesthetized rat, the action of the compounds of this invention in inhibiting the vasodilator action of histamine can also be demonstrated. The level of activity of the compounds of this invention is illustrated by the effective dose producing 50% inhibition of gastric acid secretion in the anaesthetized rat and the dose producing 50% inhibition of histamine-induced tachycardia in the isolated guinea pig atrium.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula 2 by standard procedures, for example by treating the base with an acid in a lower alkanol or by the use of ion exchange resins to form the required salt either directly from the base or from a different addition salt.

Pharmaceutical compositions comprising a pharmaceutical carrier and a compound of Formula 2 or a pharmaceutically acceptable acid addition salt thereof and methods of blocking histamine $H_2$-receptors which comprise administering to an animal a compound of Formula 2 or a pharmaceutically acceptable acid addition salt thereof are also objects of this invention. The pharmaceutical carrier employed may be, for example, either a solid or liquid. Exemplary of solid carriers are lactose, maize or potato or modified starches, dicalcium phosphate, terra alba, sucrose, celluloses, talc, gelatin, microfine silica, agar, pectin, acacia, magnesium stearate, stearic acid and the like. Exemplary of liquid carriers are syrup, peanut oil, olive oil, alcohol, propylene glycol, polyethylene glycols, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation may be in the form of a syrup, emulsion, soft gelatin capsule, sterile injectable liquid or an aqueous or nonaqueous liquid suspension. Other additives such as preservatives e.g. antioxidants or antibacterials and/or flavouring or colouring agents may also be included. The liquid forms may also be prepared in soft gelatin capsules or microcapsules. The sterile solution may be prepared in ampoules, multidose vials or unit dose disposable syringes. The preparation may also be in a semisolid form such as a cream, paste, ointment or gel or a liquid or aerosol form for topical administration.

The pharmaceutical compositions are prepared by conventional techniques involving procedures such as mixing, granulating and compressing or dissolving the ingredients as appropriate to the desired preparation. The active ingredient will be present in the compositions in an effective amount to block histamine $H_2$-receptors. The route of administration may be oral or parenteral.

Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administration, for example as a tablet, capsule, injectable solution or as a cream or ointment for topical application.

This invention is illustrated but in no way limited by the following examples, wherein all temperatures are in degrees Centigrade:

EXAMPLE 1

1,3-bis-[N-(2-(3-methoxy-2-pyridylmethylthio)ethyl) guanidino]propane

Treatment of 2-(3-methoxy-2-pyridylmethylthio)ethylamine with benzoyl isothiocyanate in refluxing chloroform and subsequent alkylation with methyl iodide yields S-methyl-N-benzoyl-N'-[2-(3-methoxy-2-pyridylmethylthio)-ethyl] isothiouronium iodide. Conversion of this compound to the corresponding sulphate on an ion-exchange column and subsequent reaction of at least a two molar excess of the product with 1,3-diaminopropane followed by hydrolytic removal of the N-benzoyl substituents with aqueous potassium carbonate at 60°–70° gives the title product.

EXAMPLE 2

When S-methyl-N-benzoyl-N'-[2-(3-methoxy-2-pyridylmethylthio)ethyl] isothiouronium sulphate is reacted according to the procedure of Example 1 with the following diamines:
(a) 1,2-diaminoethane
(b) 1,4-diaminobutane and
(c) 1,8-diaminooctane and the N-benzoyl substituents hydrolytically removed, the following products are respectively obtained:
(a) 1,2-bis [N-(2-(3-methoxy-2-pyridylmethylthio)ethyl)guanidino]ethane,
(b) 1,4-bis- [N-(2-(3-methoxy-2-pyridylmethylthio)ethyl)guanidino]butane and
(c) 1,8bis- [N-(2-(3-methoxy-3-pyridylmethylthio)ethyl)guanidine]octane.

EXAMPLE 3

1,3-bis-[N-(2-(3-ethoxy-2-pyridylmethylthio)ethyl)guanidino]propane

When in the procedure of Example 1,2-(3-ethoxy-2-pyridylmethythio)ethylamine is used in place of 2-(3-methoxy-2-pyridylmethylthio)ethylamine, the title compound is obtained.

EXAMPLE 4

Replacement as starting material in Example 1 of 2-(3-methoxy-2-pyridylmethylthio)ethylamine by
(a) 2-(3-chloro-4-methoxy-2-pyridylmethylthio) ethylamine or
(b) 2-(3,4-dimethoxy-2-pyridylmethylthio)ethylamine yields respectively the following products:
(a) 1,3-bis-[N-(2-(3-chloro-4-methoxy-2-pyridylmethylthio)ethyl)guanidino]propane and
(b) 1,3-bis-[N-(2-(3,4-dimethoxy-2-pyridylmethylthio)ethyl)guanidino]propane

EXAMPLE 5

Reaction of S-methyl-N-benzoyl-N'-[2-(3-methoxy-2-pyridylmethylthio)ethyl]isothiouronium sulphate with excess of 1,3-diamino-propane yields 3-[N-(2-(3-methoxy-2-pyridylmethylthio)ethyl) guanidino] propylamine. Reaction of this compound with the following S-methyl-N-benzoyl-isothiouronium iodides (obtained from the corresponding thioureas as hereinbefore generally described) in refluxing isopropanol:
(a) S-methyl-N-benzoyl-N'-[2-(5-methyl-4-imidazolylmethylthio)ethyl]-isothiouronium iodide,
(b) S-methyl-N-benzoyl-N'-[2-(4-imidazolylmethylthio)ethyl]isothiouronium iodide,
(c) S-methyl-N-benzoyl-N'-[2-(5-bromo-4-imidazolylmethylthio)ethyl]-isothiouronium iodide,
(d) S-methyl-N-benzoyl-N'-[4-(4-imidazolyl)butyl-]isothiouronium iodide,
(e) S-methyl-N-benzoyl-N'-[2-(2-thiazolylmethylthio)ethyl]isothiouronium iodide,
(f) S-methyl-N-benzoyl-N'-[2-(3-isothiazolylmethylthio)ethyl]isothiouronium iodide,
(g) S-methyl-N-benzoyl-N'-[2-(2-pyridylmethylthio)ethyl]isothiouronium iodide,
(h) S-methyl-N-benzoyl-N'-[2-(3-methyl-2-pyridylmethylthio)ethyl]-isothiouronium iodide,
(i) S-methyl-N-benzoyl-N'-[2-(3-hydroxy-2-pyridylmethylthio)ethyl]-isothiouronium iodide or
(j) S-methyl-N-benzoyl-N'-[2-(3-chloro-2-pyridylmethylthio)ethyl]-isothiouronium iodide
results, after hydrolytic removal of the N-benzoyl groups, respectively in the following products:
(a) 1-[N-(2-(3-methoxy-2-pyridylmethylthio)ethyl)-guanidino]-3-[N'-(2-(5-methyl-4-imidazolylmethylthio)ethyl)guandino]-propane,
(b) 1-[N-(2-(3-methoxy-2-pyridylmethylthio)ethyl)-guanidino]-3-[N'-(2-(4-imidazolylmethylthio)ethyl)guanidino]propane,
(c) 1-[N-(2-(3-methoxy-2-pyridylmethylthio)ethyl)-guanidino]-3-[N'-(2-(5-bromo-4-imidazolylmethylthio)ethyl)guanidino]propane,
(d) 1-[N-(2-(3-methoxy-2-pyridylmethylthio)ethyl)-guanidino]-3-[N'-(4-(4-imidazolylbutyl)guanidino]propane,
(e) 1-[N-(2-(3-methoxy-2-pyridylmethylthio)ethyl)-guanidino]-3-[N'-(2-(2-thiazolylmethylthio(ethyl)-guanidino]propane,
(f) 1-[N-(2-(3-methoxy-2-pyridylmethylthio)ethyl)-guanidino]-3-[N'-(2-(3-isothiazolylmethylthio)ethyl)guanidino]propane,
(g) 1-[N-(2-(3-methoxy-2-pyridylmethylthio)ethyl)-guanidino]-3-[N'-(2-(2-pyridylmethylthio)ethyl)-guanidino]propane,
(h) 1[N-(2-(3-methoxy-2-pyridylmethylthio)ethyl)-guanidino]-3-[N'-(2-(3-methyl-2-pyridylmethylthio)ethyl)guanidino]propane,
(i) 1-[N-(2-(3-methoxy-2-pyridylmethylthio)ethyl)-guanidino]-3-[N'-(2-(3-hydroxy-2-pyridylmethylthio)ethyl)guanidino]propane and
(j) 1-[N-(2-(3-methoxy-2-pyridylmethylthio)ethyl)-guanidino]-3-[N'-(2-(3-chloro-2-pyridylmethylthio)ethyl)guanidino]propane.

EXAMPLE 6

Treatment of 2-(3-methoxy-2-pyridylmethylthio)ethylamine with carbon disulphide and alkylation of the product with methyl iodide gives S-methyl-N-[2-(3-methoxy-2-pyridylmethylthio)ethyl]dithiocarbonate. When this compound (in at least two molar excess) is refluxed in ethanol with 1,3-diaminopropane the product is 1,3-bis-[N-(2-(3-methoxy-2-pyridylmethylthio)ethyl)thioureido]propane.

Similarly use of 1,4-diaminobutane or 1,8-diaminooctane in place of 1,3-diaminopropane yields respectively 1,4-bis-[N-(2-(3-methoxy-2-pyridylmethylthio)ethyl)-thioureido]butane and 1,8-bis-[N-(2-(3-methoxy-2-pyridylmethylthio)ethyl)-thioureido]octane.

EXAMPLE 7

(i) A solution of 2-(3-methoxy-2-pyridylmethylthio)ethylamine (2.1g) in ethanol (15 ml) was added over one hour to a stirred solution of dimethyl-N-cyanodithioimidocarbonate (1.5g) in ethanol (15 ml) and the mixture was allowed to stand overnight, to yield on recrystallisation from ethanol/ether N-cyano-N'-[2-(3-methoxy-2-pyridylmethylthio)ethyl]-S-methylisothiourea (2.2g), m.p. 102°–103° C.

(ii) N-Cyano-N'-[2-(3-methoxy-2-pyridylmethylthio)ethyl]-S-methylisothiourea is added to an excess of 1,3-diaminopropane and stirred at room temperature for 12 hours to yield, after chromatography N-cyano-N'-(3-aminopropyl)-N''-[2-(3-methoxy-2-pyridylmethylthio)ethyl]guanidine. Refluxing this aminopropyl guanidine in isopropanol with
(a) S-methyl-N-benzoyl-N'-[2-(3-methoxy-2-pyridylmethylthio)ethyl]isothiouronium sulphate,
(b) N-cyano-N'-[2-(3-methoxy-2-pyridylmethylthio)ethyl]-S-methylisothiourea gives respectively
(a) 1-[N-cyano-N'-(2-(3-methoxy-2-pyridylmethylthio)ethyl)guanidino]-3-[N-(2-(3-methoxy-2-pyridylmethylthio)ethyl)guanidino]propane (after alkaline hydrolytic removal of the N-benzoyl group) and (b) 1,3-bis-[N-cyano-N'-(2-(3-methoxy-2-pyridylmethylthio)ethyl)guanidino]propane.

EXAMPLE 8

1,3-bis-[1-(2-(3-methoxy-2-pyridylmethylthio)ethylamino)2-nitrovinyl-1-amino]propane (i) A solution of 2-(3-methoxy-2-pyridylmethylthio)ethylamine (2.1g) in methanol (33 ml) was added over 25 minutes to a stirred solution of 1-nitro-2-methylthio-2-methylsulphinylethylene (2.1g) in methanol (75 ml) at 30°. After standing for an hour the solution was concentrated to give a yellow-brown oil which was crystallised from ethanol/ether to yield 1-nitro-2-methylthio-2-[2-(3-methoxy-2-pyridylmethylthio)ethylamino]ethylene (1.9g), m.p. 87.5°–88.5°.

(ii) A solution of 1-nitro-2-methylthio-2-[2-(3-methoxy-2-pyridylmethylthio)ethylamino]ethylene (in at least two molar excess) and 1,3-diaminopropane is refluxed in ethanol. Evaporation followed by purification on an ion-exchange resin yields the title compound.

EXAMPLE 9

Treatment of 1,3-bis[N'-cyano-N''-(2-(3-methoxy-2-pyridylmethylthio)ethyl)guanidino]propane with dilute hydrochloric acid at 40° gives 1,3-bis-[N'-carbamoyl-N''-(2-(3-methoxy-2-pyridylmethylthio) ethyl)guanidino]propane.

EXAMPLE 10

(1) Dry hydrogen chloride is bubbled through a solution of 1,3-bis-[N'-(2-(3-methoxy-2-pyridylmethylthio) ethyl)thioureido]propane in methanol at 80° for 12 hours and the solvent is removed to give 1,3-bis[S-methyl-N'-(2-(3-methoxy-2-pyridylmethylthio)ethyl) isothioureido]propane tetrahydrochloride.

(2) This product is treated with (a) hydroxylamine hydrochloride and potassium bicarbonate in dry dimethylformamide or (b) methylamine in ethanol, to give (a) 1,3-bis-[N'-hydroxy-N''-(2-(3-methoxy-2-pyridylmethylthio)ethyl)guanidino]propane, or (b) 1,3-bis[N'-methyl-N''-(2-(3-methoxy-2-pyridylmethylthio)ethyl)guanidino]propane.

EXAMPLE 11

(i) Reaction of 2-chloro-3-nitropyridine with 2-(2-cyanoethyl)malonic acid diethyl ester and sodium hydride in tetrahydrofuran gives 1-(3-nitro-2-pyridyl)-1,1-bis-(carbethoxy)butyronitrile, m.p. 93.5°–94.5°, which after alkaline hydrolysis and acidification gives 2-(3-cyanopropyl)-3-nitropyridine hydrochloride 142°–145.5°. Reduction with hydrogen and palladium on charcoal gives 3-amino-2-(3-cyanopropyl)pyridine; and treatment of this with sodium nitrite and sulphuric acid and subsequent warming gives 2-(3-cyanopropyl)-3-hydroxypyridine. Methylation with methyl iodide and sodium ethoxide in dimethylsulphoxide and subsequent reduction with lithium aluminium hydride gives 4-(3-methoxy-2-pyridyl)butylamine.

(ii) Substitution of 4-(3-methoxy-2-pyridyl)butylamine for 2-(3-methoxy-2-pyridylmethylthio)ethylamine in the procedure of Example 1 yields 1,3-bis-[N-(4-(3-methoxy-2-pyridyl)butyl)guanidino]propane.

EXAMPLE 12

Treatment of 2-(3-methoxy-2-pyridylmethylthio)ethylamine with benzoyl isothiocyanate in refluxing chloroform yields N-benzoyl-N'-[2-(3-methoxy-2-pyridylmethylthio)ethyl]thiourea. The hydrobromide salt of this thiourea is refluxed with 1,3-dibromopropane in ethanol and the N-benzoyl groups removed by hydrolysis to yield 1,3-bis-[S-(N-(2-(3-methoxy-2-pyridylmethylthio)ethyl)isothioureido]propane tetrahydrobromide.

| EXAMPLE 13 | |
|---|---|
| Ingredients | Amounts |
| 1,3-bis-[N'-(2-(3-methoxy-2-pyridylmethylthio)ethyl)guanidino]propane dihydrochloride | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 14

By dissolving 50 mg of 1,3-bis-[N'-(2-(3-methoxy-2-pyridylmethylthio)ethyl)guanidino]propane dihydrochloride in 2 ml of sterile water, normal saline or buffered saline, a pharmaceutical composition suitable for parenteral administration is prepared.

Similarly, the other compounds of Formula 1 may be formulated into pharmaceutical compositions by the procedures of Examples 13 and 14. These pharmaceutical compositions are administered to a subject within the dose ranges given hereabove to block histamine $H_2$-receptors.

What is claimed is:

1. A compound of the formula

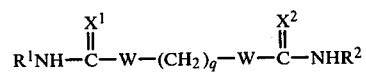

$$R^1NH-\overset{X^1}{\underset{\|}{C}}-W-(CH_2)_q-W-\overset{X^2}{\underset{\|}{C}}-NHR^2$$

wherein $X^1$ and $X^2$ are each sulphur; R' is a grouping of the structure

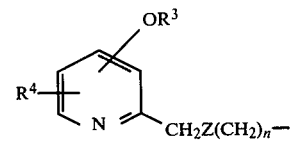

wherein $R^3$ is lower alkyl or $-(CH_2)_pA$ where p is 2 to 4, and A is hydroxy, lower alkoxy or dimethylamino; $R^4$ is hydrogen, lower alkyl, lower alkoxy, amino, halogen, or methylamino; or $-OR^3$ and $R^4$ can together form a $-O(CH_2)_bO-$group attached to adjacent carbon atoms on the pyridine ring; where b is 1 to 4; Z is sulphur or methylene; n is 2 or 3; $R^2$ is a grouping of the structure:

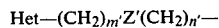

Het—$(CH_2)_{m'}Z'(CH_2)_{n'}$— wherein Het is pyrimidine, pyrazine or pyridazine which is optionally substituted by lower alkyl, hydroxy, halogen or amino; Z' is sulphur or methylene; m' is 0, 1 or 2; n' is 2 or 3 and the sum of m' and n' is 3, 4; W is NH; and q is an integer from 2 to 8 or a pharmaceutically acceptable acid addition salt thereof.

2. A compound according to claim 1 wherein Z is sulphur, n is 2 and $R^2$ is selected from a grouping of the structure Het CH$_2$S(CH$_2$)$_2$—

3. A compound according to claim 1 wherein $R^4$ is hydrogen and $R^3$ is methyl or ethyl.

4. A pharmaceutical composition to inhibit H-2 histamine receptors comprising, in an effective amount to inhibit said receptors, a compound according to claim 1 in combination with a pharmaceutically acceptable carrier.

5. A method of inhibiting H-2 histamine receptors which comprises administering orally or parenterally to an animal in need thereof in an effective amount to inhibit said receptors a compound of claim 1.

* * * * *

UNITED STATES PATENT AND TRADEMARK OFFICE
CERTIFICATE OF CORRECTION

PATENT NO. : 4,219,553

DATED : August 26, 1980

INVENTOR(S) : Graham J. Durant, Charon R. Ganellin and George S. Sach

It is certified that error appears in the above—identified patent and that said Letters Patent is hereby corrected as shown below:

On the first page of the patent, in the left-hand column, following item [62] insert:

[30] Foreign Application Priority Data

July 28, 1976    United Kingdom 31392/76

Signed and Sealed this

Twenty-fifth Day of November 1980

[SEAL]

*Attest:*

SIDNEY A. DIAMOND

*Attesting Officer*    *Commissioner of Patents and Trademarks*